United States Patent [19]

Garg et al.

[11] 4,411,766

[45] Oct. 25, 1983

[54] IRON CATALYZED COAL LIQUEFACTION PROCESS

[75] Inventors: Diwakar Garg, Macungie; Edwin N. Givens, Bethlehem, both of Pa.

[73] Assignee: Air Products and Chemicals, Inc., Allentown, Pa.

[21] Appl. No.: 352,282

[22] Filed: Feb. 25, 1982

[51] Int. Cl.$^3$ .............................................. C10G 1/06
[52] U.S. Cl. ...................................................... 208/10
[58] Field of Search ......................................... 208/10

[56] References Cited

U.S. PATENT DOCUMENTS

| | | | |
|---|---|---|---|
| 2,118,940 | 5/1938 | Pier et al. | 196/53 |
| 2,694,622 | 11/1954 | Reed et al. | 23/260 |
| 3,231,486 | 1/1966 | Perry et al. | 208/8 |
| 3,321,393 | 5/1967 | Schuman et al. | 208/10 |
| 3,505,204 | 4/1970 | Hoffman | 208/10 |
| 4,134,821 | 1/1979 | Gorin | 208/8 |
| 4,222,845 | 9/1980 | Schmid | 208/10 X |
| 4,222,846 | 9/1980 | Schmid | 208/10 X |
| 4,222,847 | 9/1980 | Carr et al. | 208/8 |
| 4,339,329 | 7/1982 | Kageyama et al. | 208/10 |

FOREIGN PATENT DOCUMENTS

| | | | |
|---|---|---|---|
| 9843 | of 1912 | Australia | 208/10 |
| 10137 | 1/1934 | Australia | 208/10 |
| 55-116794 | 3/1979 | Japan | 208/10 |
| 247584 | 6/1927 | United Kingdom | 208/10 |

OTHER PUBLICATIONS

U.S. Dept. of Energy, Exploratory Research on Solvent Refined Coal Liquefaction, Quarterly Tech. Progress Report, Jul. 1-Sep. 30, 1980. Pittsburg & Midway Coal Mining Co., DOE/ET/14800-25 Fossil Energy, February 1981.

*Primary Examiner*—William G. Wright
*Attorney, Agent, or Firm*—Geoffrey L. Chase; E. Eugene Innis; James C. Simmons

[57] ABSTRACT

A process is described for the solvent refining of coal into a gas product, a liquid product and a normally solid dissolved product. Particulate coal and a unique co-catalyst system are suspended in a coal solvent and processed in a coal liquefaction reactor, preferably an ebullated bed reactor. The co-catalyst system comprises a combination of a stoichiometric excess of iron oxide and pyrite which reduce predominantly to active iron sulfide catalysts in the reaction zone. This catalyst system results in increased catalytic activity with attendant improved coal conversion and enhanced oil product distribution as well as reduced sulfide effluent. Iron oxide is used in a stoichiometric excess of that required to react with sulfur indigenous to the feed coal and that produced during reduction of the pyrite catalyst to iron sulfide.

10 Claims, 2 Drawing Figures

IRON CATALYZED COAL LIQUEFACTION PROCESS

The government of the United States of America has rights in this invention pursuant to Contract No. DE-AC22-79ET14806 awarded by the U.S. Department of Energy.

TECHNICAL FIELD

The present invention is directed to the solvent refining of coal. More specifically, the present invention is related to the catalyzed solvent refining of coal in an upflow ebullated bed reactor. The invention is also particularly relevant to the hydrogenation of coal in the presence of hydrogen gas, a hydrogen-donor solvent and an iron catalyst.

BACKGROUND OF THE PRIOR ART

Various processes have been developed for the solvent refining of coal. Much research has gone into processes for coal liquefaction, particularly when utilizing relatively expensive metal catalysts such as those including cobalt, molybdenum, nickel and tungsten. With the increasing costs of energy and the undesirable restraints on some energy sources, there has developed heightened interest in the recovery of energy stocks in the form of liquefiable fuels from coal resources known to exist in abundance in this and other countries.

Coal liquefaction processes using expensive catalysts such as those described above have been known for quite some time. Specifically, the Germans showed great activity in this area during the war years when an internal source of liquid fuels was important to that country. A similar importance to alternate liquid fuel sources now exists throughout the world. The traditional use of expensive metal catalysts in coal liquefaction has several drawbacks. Not only are the metal catalysts expensive to provide for liquefaction processes in the first instance, but their expense dictates that additional expense is undertaken in order to provide catalyst regeneration apparatus to be used in conjunction with processes involving such catalysts.

In an attempt to overcome the problem of expensive coal liquefaction catalysts, persons skilled in this art have searched for inexpensive, potentially throw-away, catalysts which can be used in coal liquefaction processes without the need for additional apparatus necessary for regeneration. Pyrite, both as an added catalyst and as an in-situ ingredient of most coals, has been recognized as having some activity in the catalysis of coal in the liquefaction process. Other inexpensive minerals have also been shown to have catalytic activity in the coal liquefaction process.

For example, in U.S. Pat. No. 2,694,622, a catalyzed reaction of petroleum oils, coal oil or even particulate solid coal is conducted in the presence of iron and iron oxide catalysts. The iron catalysts are generally used in conjunction with water as a source of hydrogen for the hydrogenation reaction. The specification also notes that the iron oxide formed from the reaction of iron and water can also react with hydrogen sulfide to produce iron sulfides.

The use of iron oxides in a co-catalyst coal conversion process is also known in the prior art. U.S. Pat. No. 3,505,204 discloses such a process wherein iron oxide is combined as a co-catalyst with an alkali or alkaline earth metal compound and steam to produce an appropriate hydrogenation environment for the conversion of coal solids to hydrocarbons.

In U.S. Pat. No. 4,134,821, a solvent refining coal liquefaction process is described in which iron oxide catalysts are utilized in conjunction with an ebullated bed reactor. This process contemplates the use of either expensive catalysts such as cobalt and molybdenum or inexpensive catalysts such as iron oxide.

The use and reuse of inexpensive pyrite hydrogenation catalysts is set forth in U.S. Pat. No. 4,222,847 which describes a coal liquefaction process. This process discloses that a recycle pyrite catalyst shows improved activity over initially used catalysts. The specification further discloses that iron oxides under repeated recycle may experience disintegration to form ferric sulfide.

Additionally, in a February 1981 Department of Energy report by Pittsburgh and Midway Coal Mining Company, DOE/et/14800-25, the use of iron oxide and pyrite in combination as a coal liquefaction catalyst is disclosed. This disclosure was specifically in the context of a study of disposable catalysts for coal liquefaction. The disclosure notes a reduction in the catalytic activity when utilizing one to one proportions of added pyrite and added iron oxide. This prior art process fails to disclose the use of any other proportions and in fact shows decreased oil production when such a catalyst system is utilized.

The drawbacks of the prior art processes for using inexpensive, expendable catalysts in a solvent refined coal liquefaction process are overcome by the process of the present invention. The achievement of a high rate of oil production is an important aspect of the present invention. The use of inexpensive co-catalysts in a novel combination and ratio provides for unexpected catalytic activity as well as a reduction in undesirable by-products of the reaction and in the consumption of expensive hydrogen.

It is an object of the present invention to provide a coal liquefaction process which uses an inexpensive co-catalyst system of iron oxide and pyrite.

It is a further object of the present invention to use the iron oxide in a stoichiometric excess of that needed to react with all sulfur available in-situ in the reaction of the liquefying coal.

It is yet another object of the present invention to eliminate hydrogen sulfide in the coal liquefaction effluent by the appropriate addition of iron oxide to fully react with such hydrogen sulfide.

It is another object of the present invention to increase the recovery of valuable oils from a coal liquefaction process by the use of a co-catalyst of iron oxide and iron sulfide in which the iron oxide is in a stoichiometric excess of that required to react with available sulfur.

It is a further object of the present invention to reduce the consumption of hydrogen in the coal liquefaction reaction.

It is yet another object of the present invention to decrease the amount of hydrocarbon gases produced in the coal liquefaction reaction.

These and other objects will be realized and more fully understood in the description of the invention which follows.

BRIEF SUMMARY OF THE INVENTION

The subject invention is directed to a coal liquefaction process utilizing a solvent refining technique with a low cost, expendable co-catalyst system. The process generates hydrocarbon gas, liquid hydrocarbons and normally solid dissolved coal from a feed coal wherein particulate coal in a suspension of hydrogen-donor solvent is reacted in a reaction zone having a reducing atmosphere of hydrogen gas in the presence of a combination of co-catalysts of iron oxide and pyrite in which the iron as iron oxide is in a stoichiometric excess of that needed to react with substantially all sulfur available in-situ in the reaction zone so as to produce additional iron sulfide catalysts, to eliminate substantially all of the hydrogen sulfide in the reactor effluent, to increase the quantity of oil in the product distribution and to reduce SRC sulfur, hydrocarbon gas production and hydrogen consumption.

Preferably, the solvent refining reaction is performed in an upflow ebullated bed reactor wherein the bed consists of particulate coal and the co-catalysts.

Additionally, the hydrogen-donor solvent may be regenerated in-situ by the presence of hydrogen gas in the reaction zone under high pressure:

Preferably, the reaction will be conducted with an iron oxide co-catalyst chosen from the group consisting of $Fe_2O_3$ or hematite, $Fe_3O_4$ or magnetite, $FeO$ or ferrous oxide, $2Fe_2O_3.3H_2O$ or $Fe_2O_3.2Fe(OH)_3$ or limonite and $FeCO_3$ or siderite.

In a preferred embodiment of the subject invention the catalyst particle size of the pyrite and iron oxide is sufficient such that the co-catalysts are retained in the reaction zone for a residence time approximating their active catalyst life before eventually passing overhead with coal solvent effluent.

Preferably the co-catalysts are present in the reaction zone in a concentration of 5 to 50 $lb/ft^3$.

DETAILED DESCRIPTION OF THE INVENTION

Figure 1:
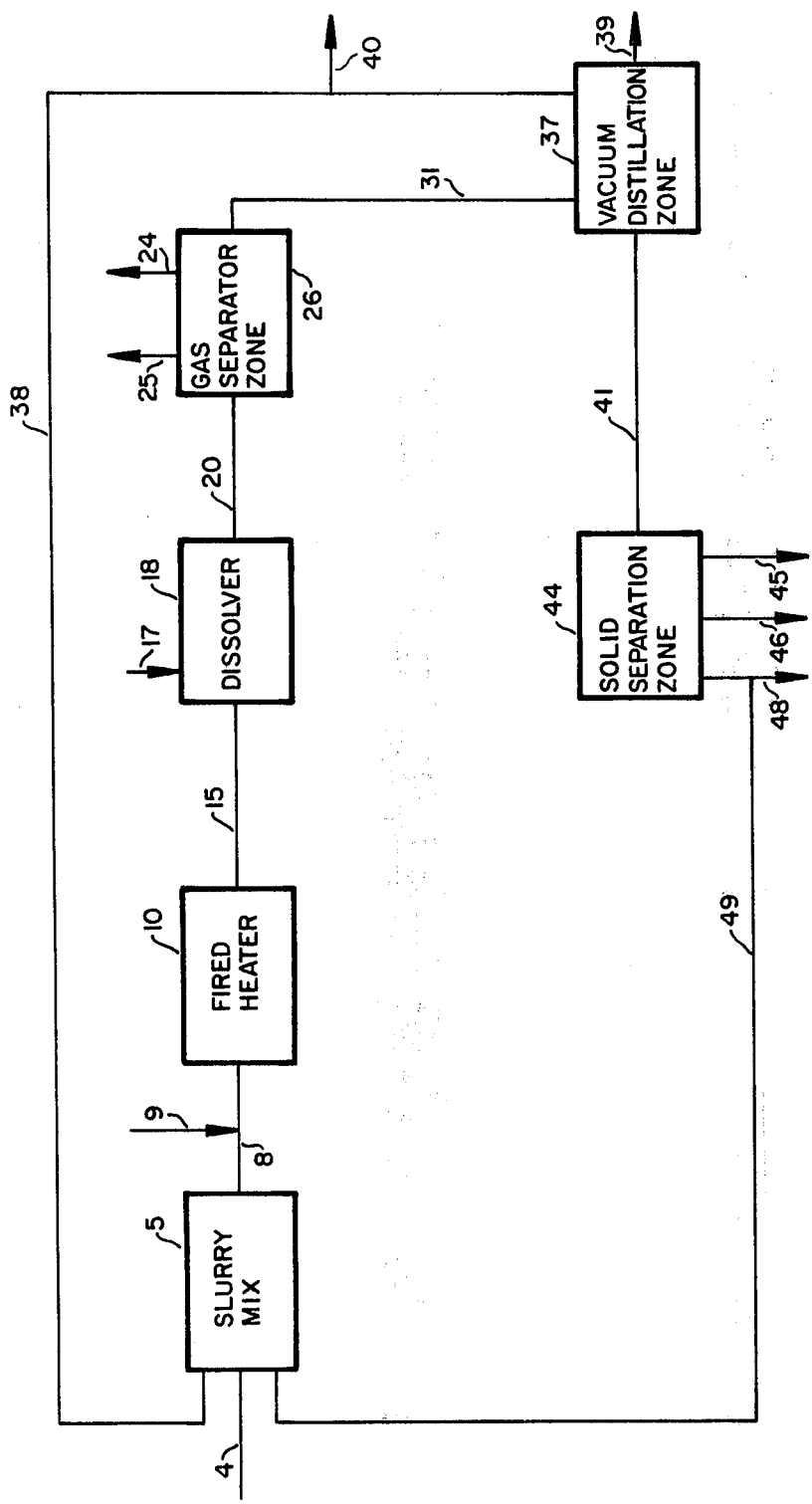
FIG. 1 constitutes an outline flowscheme of a preferred embodiment of a process for practicing the present invention.

The subject coal liquefaction process can be used with various grades of coal such as bituminous, subbituminous or lignite. These coals can be directly used or they may be processed to remove excessive rock and mineral matter by methods known to those versed in the art of coal preparation. The feed coals should be dried and ground to appropriate particle sizes or in some cases the coal may be used directly in the coal liquefaction process reactor. Preferably, the coal is predried to reduce moisture levels to those adequately handled in coal slurry equipment.

This particular coal liquefaction process uses a coal solvent and a pyrite co-catalyst in the presence of an iron-oxide co-catalyst, preferably an inexpensive naturally occurring mineral iron oxide. The term iron oxide is used herein to include compounds chosen from the group consisting of: $Fe_2O_3$ such as hematite, $Fe_3O_4$ such as magnetite, FeO (ferrous oxide), $2Fe_2O_3.3H_2O$ or $Fe_2O_3.2Fe(OH)_3$ such as limonite and $FeCO_3$ such as siderite. Elemental iron can also be contemplated. This system has been found to produce higher oil yields, that is liquid hydrocarbons, and more effective conversion of coals subject to the solvent refining liquefaction process. The important aspect of this liquefaction process over those of the prior art is the fact that iron oxide and pyrite co-catalysts, when mixed in a solvent refining reaction medium at appropriate temperature and pressure, will react and form a reduced, highly active iron sulfide catalyst most probably in the form of pyrrhotite, triolite or other iron sulfide compound structure having a formula $Fe_{1-x}S$ where $0 \times 1$. It is particularly appropriate to the present invention when both the pyrite and the iron oxide are of a specific particle size such that during their interreaction in the solvent refining reaction zone, they will generate iron sulfide of a similar particle size.

The ratio of iron oxide to pyrite which is added to the reaction zone as a co-catalyst system is a unique feature of the subject process and is of utmost importance to achieving the improved results as stated above, namely; increased oil production and reduction in hydrocarbon gas production. In addition, it has been found that the proper combination of these co-catalysts reduces and can eliminate the hydrogen sulfide by-products in the liquefaction effluent. The iron oxide and pyrite ratio should be regulated such that a stoichiometric excess of iron as iron oxide is provided over that which would be necessary to react with sulfur produced from indigenous sulfur minerals in the coal, the sulfur released from the pyrite co-catalyst in its conversion during reaction from pyrite to reduced forms such as pyrrhotite and particularly from any sulfur which becomes bound to hydrogen during the liquefaction reaction in the form of hydrogen sulfide, such as sulfur released from organic sulfur constituents of the coal being processed. Since sulfur as hydrogen sulfide is generated from the pyrite co-catalyst as well as from the mineral content of the coal and since iron species derived from iron oxides go readily to iron sulfide under the reducing conditions which exist during the solvent refining reactor operation, the generated hydrogen sulfides tend to be scrubbed from the system and more particularly from the product effluents by the addition of the stoichiometric excess of iron oxides. These reactions can be described as follows:

$FeS_2 + (1-x)H_2 \rightarrow FeS_{(1+x)} + (1-x)H_2S$

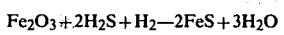

$Fe_2O_3 + 2H_2S + H_2 \rightarrow 2FeS + 3H_2O$

The entrapment of the in-situ generated hydrogen sulfide from the gas phase of the reaction zone keeps this material from exiting the reactor and considerably reduces problems in corrosion and in the size of the gas clean-up system normally found in the downstream portions of a coal liquefaction process. In addition, this novel combination of catalysts results in increased quantities of the active forms of iron sulfide being present in the reaction zone, must presumably being in the form of pyrrhotite or triolite.

In the preferred embodiment of the present invention, the process will be performed in a reactor which is in an ebullated state to the point where the reactor bed may be completely suspended. The ebullated bed should be at least 10% expanded over the settled state of the reaction bed. The reaction bed consists of particulate catalysts through which the dissolved coal and the coal solvent flow in an upstream manner.

The size of the co-catalyst particles to be employed in the reaction process of the subject invention is dependent upon several factors which may vary from system to system such as the reactor diameter, the density of the catalyst and the flow rate of the reaction medium. The upper limit of effective particle size is determined by the onset of particle settling in the reactor. The retention time of co-catalyst particles in the reactor is affected by several factors including the concentration of fresh catalysts in the feed stream. Because of the use of a disposable co-catalyst system in the present invention, the subject process will realize the benefits of a selective catalytic reaction without the concomitant disadvantage of rapid catalyst deactivation or the requirements for the recycle or regeneration of an expensive metal containing catalyst.

The reasons for catalyst deactivation are not presently well understood. However, two primary causes are probably: blocking of the active sites on the catalyst surface by mineral matter contained in the coal and carbon deposition on the catalyst surface resulting from exposure of the catalyst to very hydrogen-deficient molecules, which results from initial coal dissolution. If such catalysts are retained within the reactor for extended periods of time, the catalyst looses a significant amount of its initial activity in the first period of operation. By the use in the present invention of inexpensive, disposable catalysts such as iron oxide and pyrite, the extreme catalyst costs can be alleviated. In addition, in the preferred mode of operation with an ebullated bed, the catalyst particles are in a constant state of motion and the ash and mineral matter inherently found in coal are able to continually abrade and wash the external surfaces of the catalysts and therefore provide extended catalyst effectiveness.

A specific preferred embodiment will now be described with reference to FIG. 1. Particulate coal along with pyrite-iron oxide catalyst are passed to a slurry mix zone 5 through line 4 where the materials are slurried with a pasting solvent that may be a coal derived oil, obtained in the coking of coals in a slot oven, commonly referred to as creosote oil, anthracene oil or of equivalent type, or the solvent may be a process derived solvent having a boiling range of about 350° to 1,000° F. The slurry mix tank can be maintained at temperatures from ambient to 450° F. by controlling the temperature of the distillate solvent recycled from the vacuum distillation section 37 through line 38 and the residual SRC materials recycled from the solids separation zone 44 through line 49. In the slurry mix tank, moisture entrained in the feed coal may be removed if desired by maintaining the temperature in the tank at an elevated level while allowing the moisture to escape as steam. The slurry from the slurry mix tank 5 is passed to a pumping unit which is not shown that forces the slurry into a system maintained at high pressures of from 500 to 3,200 psig in line 8. The high pressure slurry in line 8 is then mixed with hydrogen rich gas in line 9 at a ratio of from 1,000 to 40,000 SCF per ton of feed coal. The three phase gas/slurry stream is then introduced into a preheater system 10 where the temperature is rapidly increased. The preheater system comprises a tubular reactor having a length to diameter ratio greater than 200 and more preferably greater than 500. The temperature of the three phase mixture is increased from the approximate temperature in the slurry tank to an exit temperature of 600° to 850° F. The exit slurry in line 15 from the preheater 10 which contains little undissolved coal, thereby enters the dissolver vessel 18. At this point, additional fresh hydrogen rich gas can be introduced through line 17 into the dissolver vessel 18. During the passage of the slurry through the system the viscosity changes considerably. In the preheater section the viscosity of the slurry forms a gel like material which shortly thereafter diminishes sharply in viscosity to a relatively free flowing fluid. This fluid then enters the dissolver where additional changes occur.

The preheated slurry now in the dissolver vessel undergoes various catalytic reactions. The size of the dissolver vessel is considerably larger than that employed in the preheater section of the system. The coal and recycle solvent undergo a number of chemical transformations in the dissolver vessel including, but not necessarily limited to: further dissolution of the coal in the liquid, hydrogen transfer from the recycled solvent to the coal, rehydrogenation of recycle solvent, removal of heteroatoms (S, N, O) from the coal and recycle solvent, reduction of certain components of the coal ash, such as pyrite to pyrrhotite and hydrocracking of heavy coal liquids. It is in this dissolver vessel that the novel co-catalyst system of iron oxide and pyrite, in which the iron oxide is in a stoichiometric excess of that necessary to capture all of the liberated sulfur, performs the catalytic action upon the hydrocarbonaceous materials that results in increased oil products and increased total conversion of coal while at the same time substantially completely removing hydrogen sulfide as a detrimental by-product from the reaction effluent. The indigenous mineral matter found in coal can, to a variable extent, also catalyze the above reactions. In that respect, coals from different sources will show different conversion ratios and oil distributions regardless of the catalyst system, but these results should be proportional from catalyst system to catalyst system with respect to any particular coal source.

The superficial flow through the dissolver vessel 18 will generally be at a rate from 0.003 to 0.1 feet per second for the condensed slurry phase and 0.05 to 3.0 feet per second for the gas phase. These rates are chosen to maintain good agitation in the reactor which insures good mixing. The ratio of total hydrogen gas to slurry is maintained at a level to insure an adequate hydrogen concentration in the exit slurry of at least 50 mole percent and more preferably, greater than 70 mole percent. The specific selection of flow rate through the reactor is chosen such that the coal slurry with its indigenous mineral particles move through the reactor while the catalyst particles are largely retained in the reactor. Solids will accumulate in the dissolver such that the velocity of the solids through the system is less than that of the slurry. In the preferred design, the concentration of catalyst in the feed, which also equals the concentration in the outlet during steady state operation, will be from 0.1 to 20% of the feed coal. Because of the inherent catalyst accumulation phenomena in the ebullated bed, the loading of highly active iron sulfide mineral type catalysts can be accomplished in the dissolver vessel 18. By this means, the relative amounts of iron sulfide in the dissolver at any time exceeds the amount of the catalytic component in the feed coal stream 15 being added to the reactor system.

The concentration of catalyst in the dissolver vessel 18 is a function of liquid and gas velocity, reactor height and diameter, catalyst particle size and catalyst density. Design of the overall system should give a catalyst concentration in the reactor zone or dissolver zone 18 of from 5 to 50 pounds per cubic foot.

A recycle stream of heavy bottoms recovered from the downstream apparatus, such as the separator zone 44, a vacuum distillation tower 37 or other equivalent residue rich streams found in the flow path of the liquefaction plant may be fed to the dissolver zone as recycle. Preferably, this recycle stream would be free of mineral or solid materials. As shown in the flow scheme, this recycle of heavy bottoms would be conducted from the solids separation zone 44 through line 49 to the front end of the apparatus at the slurry mix zone 5.

The dissolver zone 18 which is preferably operated as an ebullated bed is connected to the downstream equipment by line 20. The gas and slurry flow of solvent refined coal passes from the overhead of the ebullated bed in the dissolver zone 18 through line 20 into a high pressure separator system 26 in which gaseous effluent is separated from the condensed phase. This phase separation is conducted in a series of flash separating zones. The gas phase is passed from the separator zone 26 through line 24 to a gas separation and purification area, which is not shown, where hydrogen enriched gases are separated and purified and passed to the preheater section 10 and the liquefaction zone 18 through lines 9 and 17 respectively. The light gases which are recovered include hydrogen, carbon dioxide, ammonia, water and low molecular weight hydrocarbons such as methane, ethane, propane and butane. As stated above, the hydrogen can be recycled to the upstream equipment in line 9 and 17 to provide the reducing atmosphere for the coal liquefaction operation and the low molecular weight hydrocarbons may be recycled to provide fuel for temperature maintenance, such as that required in the fired heater 10.

The remaining effluent consisting of a liquid/solid slurry is then deashed. Any of the liquid/solid separation techniques known in the art may be employed, such as filtering, centrifugation, hydrocloning, solvent deashing and antisolvent deashing. Essentially all of the solid ash and undissolved coal particles are removed. Distillation may be practiced either before or after solid separation to recover recycle solvent. In the system shown in FIG. 1, the solid separation occurs downstream of the vacuum distillation zone. The liquid/solid slurry product from zone 26 is passed to a vacuum distillation zone 37 through line 31. In this stage, three streams of product are obtained; a light distillates stream with a boiling point up to 400° F., a heavy distillate stream with a boiling range of 350° F. to 1,000° F. and a solvent refined coal stream with some recycle solvent with an initial boiling point of about 850° F. The light distillate fraction is passed from the distillation zone 37 through line 39 to product storage which is not shown. The heavy distillate solvent is passed from the vacuum distillation zone 37 through line 38 as recycle to the slurry mix tank 5 and to export as product in line 40. This recycle solvent stream is recycled to the coal feed stream to help make the initial coal recycle solvent slurry. Finally, a bottoms material which contains soluble solvent refined coal, unconverted coal macerals and mineral matter is passed to the solid separation zone 44 through line 41. The solid insoluble material is removed from the solid separation zone 44 through line 45 where the solid material may be passed to a gasifier to generate hydrogen if so desired. Deashed products having various compositions, specifically high and low levels of benzene insolubles, are produced. These high and low level benzene insoluble products are passed to storage through lines 46 and 48, respectively. Part of the low level benzene insoluble product can be recycled to the slurry mix tank 5 through line 49.

Figure 2:
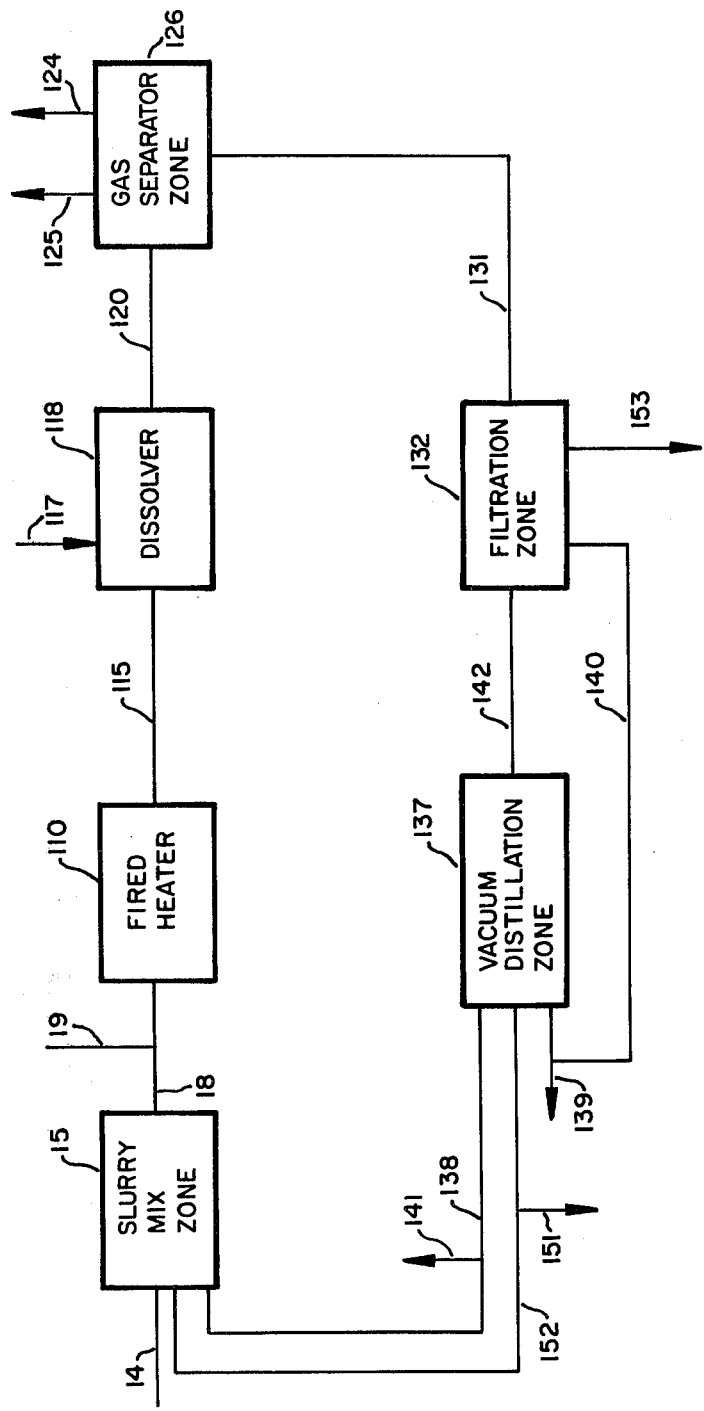
FIG. 2 consists of an outline flowscheme of an alternate embodiment of a process for practicing the subject invention.

In an alternate embodiment as shown in FIG. 2, the subject invention can be operated with the use of a filtration system for removing solids from the solvent refined coal. Coal and the pyrite-iron oxide co-catalysts are passed to the slurry mix tank 15 via line 14 where it is mixed with distillate solvent from the vacuum distillation tower 137 which is passed to the slurry mix tank through line 138. Hydrogen from line 19 is mixed with the slurry and passed through line 18 to the fired heater vessel 110. The heated slurry is passed via the transfer line 115 to a dissolver vessel 118 where additional hydrogen rich gas may be added via line 117. The dissolved three phase system is passed via line 120 into a separator zone 126 having the same capabilities as those described above in the first preferred embodiment. The slurry phase is passed via line 131 to a filtration zone 132 where a clear filtrate is obtained. A filter cake which may be washed with lighter cuts of solvent from the distillation zone 137 will be discharged via line 153. The clear filtrate and any wash solvent is passed to the vacuum distillation zone 137 via line 142. A light solvent boiling up to approximately 450° F. may be recycled to the filtration unit via line 140 or removed as a product for export in line 139. A heavier fraction can be passed to the slurry tank via line 138. Again, a portion of this fraction in line 138 may be removed as product in line 141. The vacuum bottoms which is the major SRC product may be, in part, recycled through line 152 to the slurry mix tank 15 or may be collected through line 151.

The novel co-catalyst system of the present invention, which can be utilized in the exemplary process flowschemes described above, is described in greater detail in the ensuing examples which demonstrate the significant improvement of the invention co-catalysts over the prior art catalysts. The examples are illustrative of the invention and are not meant to be a limitation of the scope of the invention.

EXAMPLE 1

This example illustrates the reaction of coal without additives. The slurry was comprised of Kentucky Elkhorn #2 coal having the composition shown in Table 1 and a process solvent having the elemental composition and boiling point distribution shown in Tables 2 and 3, respectively. A coal oil slurry (70 wt% solvent+30 wt% coal) was passed into a one-liter continuous stirred tank reactor at a total pressure of 2000 psig and a hydrogen flow rate of 20,000 SCF/T of coal. The reaction temperature was 850° F. and the nominal residence time was 40 min. The reaction product distribution obtained was as shown in Table 5. The conversion of coal was 84.3% and the oil yield was 8.3% based on moisture-ash-free (maf) coal. The sulfur content of the residual hydrocarbon fraction (SRC) was 0.55 percent and the hydrogen consumption was 0.73 wt% of maf coal. The oil yield in Table 5 constitutes the valuable liquid hydrocarbon product sought from the solvent refining of coal.

TABLE 1

| Analysis of Elkhorn #2 Coal | |
|---|---|
| | Weight % |
| Proximate Analysis | |
| Moisture | 1.55 |
| Dry Ash | 6.29 |

TABLE 1-continued

Analysis of Elkhorn #2 Coal

| | Weight % |
|---|---|
| Ultimate Analysis | |
| C | 77.84 |
| H | 5.24 |
| O | 7.20 |
| N | 1.75 |
| S | 1.08 |
| Distribution of Sulfur | |
| Total Sulfur | 1.08 |
| Sulfate Sulfur | 0.04 |
| Pyritic Sulfur | 0.25 |
| Organic Sulfur | 0.79 |

TABLE 2

Elemental Composition of Solvent

| Element | Weight % |
|---|---|
| Carbon | 89.7 |
| Hydrogen | 7.2 |
| Oxygen | 1.4 |
| Nitrogen | 1.1 |
| Sulfur | 0.6 |
| Number Average Molecular Weight | 208 |
| NMR Distribution of Hydrogen, % | |
| $H_{Aromatic}$ | 44.4 |
| $H_{Benzylic}$ | 28.0 |
| $H_{Other}$ | 27.6 |

TABLE 3

Simulated Distillation of Solvent

| Weight % Off | Temperature, F. |
|---|---|
| I.B.P. | 519 |
| 5 | 548 |
| 10 | 569 |
| 20 | 590 |
| 30 | 607 |
| 40 | 627 |
| 50 | 648 |
| 60 | 673 |
| 70 | 699 |
| 80 | 732 |
| 90 | 788 |
| 95 | 835 |
| 98 | 878 |
| F.B.P. | 911 |

EXAMPLE 2

This example illustrates the catalytic effect of pyrite. The coal and solvent feed slurry described in Example 1 was combined with pyrite in three runs (A, B and C) at three concentration levels of 2.5, 5.0 and 10.0 wt. percent of slurry with the solvent wt. percent reduced accordingly. These slurries were processed at the same reaction conditions described in Example 1. The pyrite was obtained from the Robena Mine at Angelica, Pa. and is described in Table 4. The product distributions obtained are shown in Table 5. Conversion of coal and oil yield were consistently higher in the presence of pyrite than shown in Example 1. The SRC sulfur generally decreased on addition of pyrite except at higher concentrations. The hydrogen consumption was significantly higher with pyrite than without pyrite (see Example 1). The x-ray diffraction analysis of residue from the liquefaction reaction showed complete conversion of pyrite to pyrrhotite. These three runs show that the catalytic effect of pyrite is insensitive to catalyst concentration over the range tested.

TABLE 4

Analysis of Robena Pyrite

| | Weight % |
|---|---|
| C | 4.5 |
| H | 0.3 |
| N | 0.6 |
| S | 41.3 |
| O | 6.0 |
| Fe | 42.3 |
| Sulfur Distribution | |
| Pyritic | 40.4 |
| Sulfate | 0.7 |
| Organic | 0.6 |
| Other Impurities | |
| Al, Si, Na, Mn, V, Ti, Cr, Sr, Pb, Co, Mg, Mo, Cu, and Ni | |

EXAMPLE 3

In this example the catalytic activity of reagent grade $Fe_2O_3$ obtained from Fisher Scientific Company is illustrated. The coal and solvent described in Example 1 were combined with the iron oxide in two runs (A and B) at two different concentration levels to give slurry compositions of 1.7 and 3.4 wt. percent of $Fe_2O_3$ with the wt. percent of solvent reduced accordingly. These slurries were processed at the same reaction conditions described in Example 1. The product distributions obtained from processing these two slurries at conditions the same as in Example 1 are shown in Table 5. Higher conversion of coal and oil yield were obtained at both levels of $Fe_2O_3$ than shown in Example 1. The SRC sulfur decreased slightly and the hydrogen consumption was not changed significantly on addition of $Fe_2O_3$ (see Example 1.). All the $H_2S$ generated in the reaction was scrubbed out by $Fe_2O_3$ since no $H_2S$ was observed in the gaseous effluent. The x-ray diffraction analysis of residue from the liquefaction reaction showed the $Fe_2O_3$ was completely converted to a mixture of $Fe_3O_4$, FeS and pyrrhotite. As for pyrite in Example 2 above, this experiment tends to show that the reaction is insensitive to $Fe_2O_3$ catalyst concentration over the range tested.

EXAMPLE 4

This example illustrates the catalytic activity of a mixture of reagent grade $Fe_2O_3$ described in Example 3 and pyrite described in Example 2. The coal and solvent described in Example 1 were combined with a mixture of reagent grade $Fe_2O_3$ and pyrite in three runs (A, B and C) at three different concentration levels of feed slurry, respectively, as shown in Table 5: 0.5 wt.% $Fe_2O_3$ and 0.75 wt.% pyrite; 1.7 wt.% $Fe_2O_3$ and 2.5 wt.% pyrite; 3.4 wt.% $Fe_2O_3$ and 5.0 wt.% pyrite with the solvent wt. percent reduced accordingly. These slurries were processed at the same conditions described in Example 1. The product distribution obtained is described in Table 5.

Run A of Example 4 approximates the disclosed experiments of Pittsburgh and Midway Coal Mining, specifically run DOE 373, the results of which appear in Table 6. Both Run A of the present invention's Example 4 and DOE 373 use a combination of $Fe_2O_3$ and pyrite to catalyze the solvent refining reaction. However, the amount used is in a ratio of less than a stoichiometric amount of Fe as $Fe_2O_3$ to react with in-situ and catalyst generated $H_2S$. The result is that the oil yields of both Run 4A and DOE 373 are no better than pyrite catalyzed reactions. However, when greater than stoichiometric amounts of Fe as $Fe_2O_3$ to Fe as $FeS_2$ are used, as in Runs 4B and 4C of the present invention's Example 4, significant oil yields above Run 4A and DOE 373 were unexpectedly obtained and all of the $H_2S$ was eliminated from the effluent of the reactor. The oil yield was higher at the higher combined concentration of $Fe_2O_3$ and pyrite in the feed slurry (see Table 5). In Runs 4B and 4C, all the $H_2S$ generated by reduction of pyrite and desulfurization of coal was scrubbed out by $Fe_2O_3$ since no $H_2S$ was observed in the effluent gas stream. The x-ray diffraction analysis of residue from the liquefaction reaction showed complete conversion of $Fe_2O_3$ and pyrite mixture to a mixture of $Fe_3O_4$, FeS and pyrrhotite.

As can be seen in the results listed in Table 5, the mere increase in overall Fe containing catalyst species is not the key to the improved catalytic effect and attendant improved liquefaction products demonstrated in the present invention. A comparison of Example 2B, wherein pyrite catalyst alone contributes an overall Fe content of 7.02 wt %, and Example 4B, wherein the co-catalysts of pyrite and iron oxide contribute a combined Fe content of 7.59 wt%, indicates that despite substantially similar concentrations of Fe as catalyst, remarkably different oil yields are observed. Example 2B has a 24.2 wt % oil yield, while Example 4B has a 28 wt % oil yield.

Similarly, a review of Example 2C, using pyrite catalyst alone with an Fe concentration of 13.82 wt %, and Example 4C, using the combined co-catalysts of pyrite and iron oxide with an Fe concentration of 14.96 wt %, indicates again that despite similar concentrations of Fe as catalyst remarkably different oil yields are observed. Example 2C has a 27.0 wt % oil yield, while Example 4C has a 38.6 wt % oil yield.

A comparison of the two sets of examples (2B and 2C against 4B and 4C) indicates that for a comparable increase in the concentration of Fe as catalyst the prior art obtains only a small increase in oil product, while the examples of the present invention obtain a dramatic 10 wt % increase in oil production at a higher overall oil yield as a base production rate (i.e. 28.0 wt %).

These same sets of examples show a favorable reduction in the undesirable production of hydrocarbon gases (HC) in a comparison of the runs of the present invention 4B and 4C when viewed with respect to the prior art pyrite runs 2B and 2C. A similar comparison can be made with respect to the reduction in consumption of expensive hydrogen.

The product data of runs 4B and 4C are also favorable to the iron oxide catalyst runs 3A and 3B in the hydrocarbon (HC) and hydrogen ($H_2$) categories when consideration is made of the dramatic difference in the extent to which coal is converted to oils in the runs of the present invention and those runs of the prior art iron oxide. As more complete conversion is made, unavoidable consumption of hydrogen is expected and hydrocarbon gas production increases would also be probable. The fact that for considerable differences in the extent of coal conversion to oil, the resulting data shows similar hydrocarbon gas production and close approximate consumption in hydrogen when Examples 3A and 3B are compared to Examples 4B and 4C is demonstrative of a significant improvement in the liquefaction reaction using the catalyst system of the present invention.

TABLE 5

|  | Example 1 | Example 2A | Example 2B | Example 2C | Example 3A | Example 3B | Example 4A | Example 4B | Example 4C |
|---|---|---|---|---|---|---|---|---|---|
| Catalyst | None | Pyrite | Pyrite | Pyrite | $Fe_2O_3$ | $Fe_2O_3$ | Pyrite/$Fe_2O_3$ | Pyrite/$Fe_2O_3$ | Pyrite/$Fe_2O_3$ |
| Catalyst Concentration, wt. % slurry | — | 2.5 | 5.0 | 10.0 | 1.7 | 3.4 | 0.75/0.50 | 2.5/1.7 | 5.0/3.4 |
| Yield, wt. % MAF Coal |  |  |  |  |  |  |  |  |  |
| $H_2S^a$ | 0.2 | 2.3 | 3.4 | 7.1 | 0.0 | 0.0 | 0.1 | 0.0 | 0.0 |
| HC | 7.0 | 10.2 | 10.0 | 10.6 | 4.7 | 6.5 | 7.3 | 5.8 | 5.9 |
| $CO + CO_2$ | 0.6 | 0.9 | 1.0 | 1.2 | 0.6 | 0.6 | 1.0 | 0.8 | 0.7 |
| Oil | 8.3 | 25.5 | 24.2 | 27.0 | 23.8 | 22.6 | 24.9 | 28.0 | 38.6 |
| Asphaltene | 21.6 | 22.3 | 18.6 | 22.2 | 18.9 | 19.1 | 24.0 | 24.1 | 21.6 |
| Preasphaltene | 43.4 | 28.2 | 32.3 | 25.6 | 35.1 | 35.7 | 29.6 | 29.8 | 20.0 |
| SRC | 65.0 | 50.5 | 50.9 | 47.8 | 54.0 | 54.8 | 53.6 | 53.9 | 41.6 |
| Water | 3.1 | 3.2 | 3.5 | 4.0 | 3.3 | 2.3 | 1.4 | 2.5 | 1.7 |
| Conversion | 84.3 | 90.6 | 89.6 | 90.6 | 86.4 | 86.8 | 88.1 | 91.0 | 88.3 |
| $H_2$ Consumption | 0.73 | 1.75 | 1.81 | 2.41 | 0.49 | 0.73 | 0.90 | 0.93 | 1.16 |
| SRC Sulfur | 0.55 | 0.49 | 0.51 | 0.57 | 0.48 | 0.52 | 0.30 | 0.48 | 0.48 |
| Iron Conc., wt. % Coal |  |  |  |  |  |  |  |  |  |
| Fe as $FeS_2$ in Coal | 0.22 | 0.22 | 0.22 | 0.22 | 0.22 | 0.22 | 0.22 | 0.22 | 0.22 |
| Fe as $FeS_2$ added | — | 3.40 | 6.80 | 13.60 | — | — | 1.09 | 3.40 | 6.80 |
| Total Fe as $FeS_2$ | 0.22 | 3.62 | 7.02 | 13.82 | 0.22 | 0.22 | 1.31 | 3.62 | 7.02 |
| Total Fe as $Fe_2O_3$ added | — | — | — | — | 3.97 | 7.94 | 1.17 | 3.97 | 7.94 |
| Total Fe | 0.22 | 3.62 | 7.02 | 13.82 | 4.19 | 8.16 | 2.48 | 7.59 | 14.96 |
| Fe as $Fe_2O_3$/Fe as $FeS_2$ | 0.00 | 0.00 | 0.00 | 0.00 | 18.05 | 36.10 | 0.89 | 1.10 | 1.13 |

$^a$Includes $H_2S$ derived from additive

TABLE 6

| Pittsburgh & Midway Coal Mining Company Data$^a$ | | | | |
|---|---|---|---|---|
|  | DOE 372 | DOE 373 | DOE 374 | DOE 375 |
| Catalyst | $FeS_2$ | $FeS_2/Fe_2O_3$ | $Fe_2O_3$ | None |
| Yields, wt. % MAF Coal |  |  |  |  |
| $H_2S^b$ | 2.0 | 1.0 | 0.1 | 1.2 |
| Oil | 20.1 | 18.5 | 15.7 | 16.4 |
| SRC | 57.3 | 59.3 | 61.5 | 61.4 |
| Conversion | 93.9 | 94.0 | 93.4 | 93.5 |
| $H_2$ Consumption | 2.4 | 2.4 | 2.0 | 2.0 |
| SRC Sulfur, % | 1.03 | 0.94 | 0.94 | 1.04 |
| Iron Concentration, wt. % Coal |  |  |  |  |
| Fe as $FeS_2$ in Coal | 0.79 | 0.79 | 0.79 | 0.79 |
| Fe as $FeS_2$ added | 1.89 | 0.95 | — | — |
| Total Fe as $FeS_2$ | 2.68 | 1.74 | 0.79 | 0.79 |
| Total Fe as $Fe_2O_3$ added | — | 1.41 | 2.33 | — |
| Total Fe | 2.68 | 3.15 | 3.12 | 0.79 |
| Fe as $Fe_2O_3$/Fe as $FeS_2$ | 0.0 | 0.81 | 2.95 | 0.00 |

$^a$Table 2 of DOE Report # DOE/ET/14800-25
$^b$Includes $H_2S$ derived from additive As can be seen from the preceding examples, particularly Example 4, the use of a stoichiometric excess of iron as iron oxide in conjunction with pyrite as a co-catalyst for a coal liquefaction reaction provides superior results in the generation of oil or liquid hydrocarbons in a product distribution of such a liquefaction reaction as well as positively influencing the overall conversion of the feed coal and reducing the hydrogen sulfide effluent from the overall reaction scheme. In addition, the increase in concentration of the co-catalysts when iron oxide is present in stoichiometric excess also unexpectedly positively affects the yield of oil. In Run 4B the oil yield was 28 wt.%, and when the co-catalyst concentration was increased in Run 4C the oil yield went up to a remarkable 38.6 wt.%.

This dramatic result would not be expected from the prior art. Examples 2A, 2B, 2C and 3A, 3B show that with either pyrite or iron oxide catalysts individually the oil yield is insensitive to concentration of catalyst. Therefore, it would be unexpected that when the co-catalysts of iron oxide and pyrite are used in the reaction, that concentration would have a direct effect on the reaction product, particularly oil yield.

The stoichiometric excess of iron as iron oxide to iron as pyrite also provides high total coal conversions and reduced SRC sulfur and hydrocarbon gas formation, as well as eliminating $H_2S$ in the coal effluent as shown in the data of Table 5. Hydrogen consumption is also significantly less than in the pyrite system. These beneficial results further distinguish the co-catalyst system of the present system from those of the prior art. A stoichiometric excess exists when slightly more iron as iron oxide is present as a co-catalyst with pyrite in the reaction than is required to completely scrub out all the $H_2S$ generated by: the reduction of mineral pyrite present in the coal; added pyrite co-catalyst; and organic sulfur compounds which are decomposed or removed from the coal during the reaction.

Although the preferred components of the present invention has been demonstrated with ferric oxide ($Fe_2O_3$) or hematite, it is understood that the invention can be practiced with similar success using $Fe_3O_4$ or mineral magnetite, FeO or ferrous oxide, $2Fe_2O_3.3H_2O$ or $Fe_2O_3.2Fe(OH)_3$ or limonite, and $FeCO_3$ or mineral siderite. Potentially even elemental iron can be contemplated. In that regard, it will be understood that though the invention is contemplated in its preferred format for an ebullated bed reactor and a ferric oxide/pyrite co-catalyst, in fact the reaction can be performed and the co-catalyst system would be equally relevant to other coal liquefaction processes of the catalytic type with other catalyst combinations as indicated above.

Therefore, the invention should not be deemed to be limited by the above embodiments in which particular reaction zones are contemplated and particular co-catalyst systems are set forth, but rather the scope of the invention should be determined by the claims which follow.

We claim:

1. A process for the catalytic solvent refining of coal to generate liquid hydrocarbons, hydrocarbon gas and normally solid dissolved coal from the feed coal wherein particulate coal in a suspension of hydrogen donor coal solvent is reacted in a reducing atmosphere in the presence of a combination of co-catalysts of iron oxide and pyrite in which the iron as iron oxide is in a stoichiometric excess of that needed to react with substantially all sulfur available in-situ in the reaction medium so as to product additional iron sulfide catalyst, to eliminate substantially all of the hydrogen sulfide in the reactor effluent and to increase the liquid hydrocarbon content of the product distribution.

2. The process of claim 1 wherein the solvent refining reaction is performed in an upflow ebullated bed reactor wherein the bed consists of particulate coal and co-catalysts.

3. The process of claim 1 wherein the reaction is conducted in the presence of hydrogen gas.

4. The process of claim 1 wherein the iron oxide co-catalyst is chosen from the group consisting of $Fe_2O_3$ or hematite, $Fe_3O_4$ or magnetite, FeO or ferrous oxide, $2Fe_2O_3.3H_2O$ or $Fe_2O_3.2Fe(OH)_3$ or limonite, and $FeCO_3$ or siderite.

5. The process of claim 1 wherein the iron oxide co-catalyst is present in the reaction in a stoichiometric excess of that required to bind the sulfur produced as the pyrite co-catalyst is reduced to pyrrhotite.

6. The process of claim 2 wherein the catalyst particle size of the pyrite and iron oxide co-catalysts is sufficient such that the co-catalysts are retained in the reactor for a residence time approximating their active catalyst life before being passed overhead with coal solvent effluent.

7. The process of claim 1 or 6 wherein the co-catalyst particle size is in the range of 20 to 100 mesh.

8. The process of claim 1 or 6 wherein the co-catalyst has a density of 2 to 7.9 grams per cubic centimeter.

9. The process of claim 1 wherein the co-catalyst is present in the reaction zone in a concentration of 5 to 50 lb/ft$^3$.

10. The process of claim 1 wherein elemental iron is used as a co-catalyst with pyrite.

* * * * *